(12) United States Patent
Dugger, III et al.

(10) Patent No.: US 9,078,816 B2
(45) Date of Patent: Jul. 14, 2015

(54) BUCCAL, POLAR AND NON-POLAR SPRAY CONTAINING ONDANSETRON

(75) Inventors: Harry A. Dugger, III, Flemington, NJ (US); Mohammed Abd El-Shafy, Hauppauge, NY (US)

(73) Assignee: Suda Ltd., Osborne Park (AU)

( * ) Notice: Subject to any disclaimer, the term of this patent is extended or adjusted under 35 U.S.C. 154(b) by 0 days.

(21) Appl. No.: 13/445,331

(22) Filed: Apr. 12, 2012

(65) Prior Publication Data

US 2012/0295945 A1 Nov. 22, 2012

Related U.S. Application Data

(60) Continuation of application No. 12/350,602, filed on Jan. 8, 2009, now abandoned, which is a continuation of application No. 11/429,953, filed on May 9, 2006, now abandoned, which is a division of application No. 10/671,717, filed on Sep. 29, 2003, now abandoned, which is a continuation-in-part of application No. 10/230,085, filed on Aug. 29, 2002, now abandoned, which is a continuation-in-part of application No. 09/537,118, filed on Mar. 29, 2000, now abandoned, which is a continuation-in-part of application No. PCT/US97/17899, filed on Oct. 1, 1997.

(51) Int. Cl.
*A61K 31/4178* (2006.01)
*A61K 9/08* (2006.01)
*A61K 9/00* (2006.01)
*A61K 31/573* (2006.01)
*A61K 47/10* (2006.01)

(52) U.S. Cl.
CPC .............. *A61K 9/006* (2013.01); *A61K 9/0056* (2013.01); *A61K 31/4178* (2013.01); *A61K 31/573* (2013.01); *A61K 47/10* (2013.01)

(58) Field of Classification Search
CPC . A61K 31/4178; A61K 31/573; A61K 47/10; A61K 9/006; A61K 2300/00
See application file for complete search history.

(56) References Cited

U.S. PATENT DOCUMENTS

| | | |
|---|---|---|
| 3,155,574 A | 11/1964 | Silson et al. |
| 3,304,230 A | 2/1967 | Abramson et al. |
| 3,784,684 A | 1/1974 | Bossert et al. |
| 4,495,168 A | 1/1985 | Schmolka |
| 4,689,233 A | 8/1987 | Dvorsky et al. |
| 4,704,406 A | 11/1987 | Stanislaus et al. |
| 4,755,389 A | 7/1988 | Jones et al. |
| 4,814,161 A | 3/1989 | Jinks et al. |
| 4,857,312 A | 8/1989 | Hegasy et al. |
| 4,863,720 A | 9/1989 | Burghart et al. |
| 4,863,970 A | 9/1989 | Patel et al. |
| 4,919,919 A | 4/1990 | Aouda et al. |
| 4,935,243 A | 6/1990 | Borkan et al. |
| 5,011,678 A | 4/1991 | Wang et al. |
| 5,047,230 A | 9/1991 | Nagy et al. |
| 5,128,132 A | 7/1992 | Parnell |
| 5,135,753 A | 8/1992 | Baker et al. |
| 5,143,731 A | 9/1992 | Viegas et al. |
| 5,166,145 A | 11/1992 | Jao et al. |
| 5,186,925 A | 2/1993 | Cholcha |
| 5,240,932 A | 8/1993 | Morimoto et al. |
| 5,290,540 A | 3/1994 | Prince et al. |
| 5,364,616 A | 11/1994 | Singer et al. |
| 5,370,862 A | 12/1994 | Klokkers-Bethke et al. |
| 5,428,006 A | 6/1995 | Bechgaard et al. |
| 5,456,677 A | 10/1995 | Spector |
| 5,457,100 A | 10/1995 | Daniel |
| 5,474,759 A | 12/1995 | Fassberg et al. |
| 5,502,076 A | 3/1996 | Dixit et al. |
| 5,519,059 A | 5/1996 | Sawaya |
| 5,593,684 A | 1/1997 | Baker et al. |
| 5,602,182 A | 2/1997 | Popli et al. |
| 5,605,674 A | 2/1997 | Purewal et al. |
| 5,607,915 A | 3/1997 | Patton |
| 5,635,161 A | 6/1997 | Adjei et al. |
| 5,645,856 A | 7/1997 | Lacy et al. |
| 5,719,197 A * | 2/1998 | Kanios et al. .............. 514/772.6 |

(Continued)

FOREIGN PATENT DOCUMENTS

| | | |
|---|---|---|
| DE | 3338978 A1 | 5/1984 |
| DE | 3246081 A1 | 6/1984 |

(Continued)

OTHER PUBLICATIONS

Physicians Desk Reference, 49th Edition, 1995.*
The pharmacological Basis of Therapeutics, Goodman & Gilman, 9th Edition.*
Brox et el., Studies on the growth inhibition and metabolism of 2'-deoxy-2' fluorocytidine in cultured human lymphoblasts, *Cancer Res.*, 34: 1838-42 (1974).
Cassidy et al., Controlled buccal delivery of buprenorphine, *J. Control. Rel.*, 25: 21-9 (1993).
Cosdon, Sprays sold as better way to get vitamins, *Seminole Times; Seminole Business Digest*, Nov. 6, 1996.
Drug Facts and Comparisons (Jan. 2002) pp. 186c-186d.

(Continued)

*Primary Examiner* — Mina Haghighatian
(74) *Attorney, Agent, or Firm* — Marshall, Gerstein & Borun LLP

(57) ABSTRACT

Buccal aerosol sprays or capsules using polar and non-polar solvents have now been developed which provide ondansetron for rapid absorption through the oral mucosa, resulting in fast onset of effect. The buccal polar compositions of the invention comprise formulation I: aqueous polar solvent, ondansetron, and optional flavoring agent; formulation II: aqueous polar solvent, ondansetron, optionally flavoring agent, and propellant; formulation III: non-polar solvent, ondansetron, and optional flavoring agent; formulation IV: non-polar solvent, ondansetron, optional flavoring agent, and propellant; formulation V: a mixture of a polar solvent and a non-polar solvent, ondansetron, and optional flavoring agent; formulation VI: a mixture of a polar solvent and a non-polar solvent, ondansetron, optional flavoring agent, and propellant.

3 Claims, 1 Drawing Sheet

(56) References Cited

U.S. PATENT DOCUMENTS

| | | |
|---|---|---|
| 5,766,573 A | 6/1998 | Purewal et al. |
| 5,795,909 A | 8/1998 | Shashoua et al. |
| 5,824,307 A | 10/1998 | Johnson |
| 5,869,082 A | 2/1999 | Dugger, III |
| 5,891,465 A | 4/1999 | Keller et al. |
| 5,906,811 A * | 5/1999 | Hersh .................... 424/54 |
| 5,908,611 A | 6/1999 | Gottlieb et al. |
| 5,910,301 A | 6/1999 | Farr et al. |
| 5,955,098 A | 9/1999 | Dugger, III |
| 5,981,591 A | 11/1999 | Deihl |
| 6,037,346 A | 3/2000 | Doherty, Jr. et al. |
| 6,071,539 A | 6/2000 | Robinson et al. |
| 6,110,486 A * | 8/2000 | Dugger, III .................... 424/435 |
| 6,143,329 A * | 11/2000 | Kim .................... 424/489 |
| 6,212,227 B1 | 4/2001 | Ko et al. |
| 6,258,032 B1 | 7/2001 | Hammesfahr |
| 6,271,240 B1 | 8/2001 | Simon |
| 6,299,900 B1 | 10/2001 | Reed et al. |
| 6,375,975 B1 | 4/2002 | Modi |
| 6,458,842 B1 | 10/2002 | Dickinson et al. |
| 6,512,002 B2 | 1/2003 | Lee et al. |
| 6,676,931 B2 * | 1/2004 | Dugger, III. .................... 424/45 |
| 6,706,255 B2 | 3/2004 | Dickinson et al. |
| 6,816,452 B1 | 11/2004 | Maehata |
| 6,969,508 B2 | 11/2005 | Dugger, III |
| 6,977,070 B2 | 12/2005 | Dugger, III |
| 6,998,110 B2 | 2/2006 | Dugger, III |
| 7,202,233 B2 | 4/2007 | Penkler |
| 2002/0102218 A1 | 8/2002 | Cowan |
| 2002/0110524 A1 | 8/2002 | Cowan et al. |
| 2003/0039680 A1 | 2/2003 | Dugger, III |
| 2003/0077227 A1 | 4/2003 | Dugger, III |
| 2003/0077228 A1 | 4/2003 | Dugger, III |
| 2003/0077229 A1 | 4/2003 | Dugger, III |
| 2003/0082107 A1 | 5/2003 | Dugger, III |
| 2003/0095925 A1 | 5/2003 | Dugger, III |
| 2003/0095926 A1 | 5/2003 | Dugger, III |
| 2003/0095927 A1 | 5/2003 | Dugger, III |
| 2003/0185761 A1 | 10/2003 | Dugger, III |
| 2003/0190286 A1 | 10/2003 | Dugger, III |
| 2003/0191180 A1 | 10/2003 | Ross |
| 2003/0211047 A1 | 11/2003 | Dugger, III |
| 2004/0062716 A1 | 4/2004 | Dugger, III |
| 2004/0120895 A1 | 6/2004 | Dugger, III |
| 2004/0120896 A1 | 6/2004 | Dugger, III |
| 2004/0136913 A1 | 7/2004 | Dugger, III et al. |
| 2004/0136914 A1 | 7/2004 | Dugger, III et al. |
| 2004/0136915 A1 | 7/2004 | Dugger, III et al. |
| 2004/0141923 A1 | 7/2004 | Dugger, III et al. |
| 2004/0191178 A1 | 9/2004 | Cutler |
| 2004/0265239 A1 | 12/2004 | Dugger, III et al. |
| 2005/0002867 A1 | 1/2005 | Dugger, III et al. |
| 2005/0025712 A1 | 2/2005 | Dugger, III |
| 2005/0025713 A1 | 2/2005 | Dugger, III |
| 2005/0025714 A1 | 2/2005 | Dugger, III |
| 2005/0025715 A1 | 2/2005 | Dugger, III |
| 2005/0025716 A1 | 2/2005 | Dugger, III |
| 2005/0025717 A1 | 2/2005 | Dugger, III |
| 2005/0142069 A1 | 6/2005 | Dugger, III |
| 2005/0163719 A1 | 7/2005 | Dugger, III et al. |
| 2005/0180923 A1 | 8/2005 | Dugger, III et al. |
| 2005/0281752 A1 | 12/2005 | Dugger, III |
| 2005/0281753 A1 | 12/2005 | Dugger, III |
| 2005/0287075 A1 | 12/2005 | Dugger, III |
| 2006/0159624 A1 | 7/2006 | Dugger, III et al. |
| 2006/0165604 A1 | 7/2006 | Dugger, III et al. |
| 2006/0171896 A1 | 8/2006 | Dugger, III et al. |
| 2006/0198790 A1 | 9/2006 | Dugger, III et al. |
| 2006/0210484 A1 | 9/2006 | Dugger, III et al. |
| 2006/0216240 A1 | 9/2006 | Dugger, III et al. |
| 2006/0216241 A1 | 9/2006 | Dugger, III et al. |
| 2006/0222597 A1 | 10/2006 | Dugger, III |
| 2007/0048229 A1 | 3/2007 | Dugger, III et al. |
| 2008/0170995 A1 | 7/2008 | Dugger, III |
| 2009/0118170 A1 | 5/2009 | Dugger, III |
| 2009/0123387 A1 | 5/2009 | Dugger, III |
| 2009/0124554 A1 | 5/2009 | Dugger, III |
| 2009/0131514 A1 | 5/2009 | Dugger, III |
| 2009/0162297 A1 | 6/2009 | Dugger, III et al. |
| 2009/0162298 A1 | 6/2009 | Dugger, III et al. |
| 2009/0162300 A1 | 6/2009 | Dugger, III et al. |
| 2009/0186035 A1 | 7/2009 | Dugger, III |
| 2009/0186099 A1 | 7/2009 | Dugger, III |
| 2010/0209541 A1 | 8/2010 | Dugger, III |
| 2012/0202866 A1* | 8/2012 | Dugger et al. .................... 514/397 |

FOREIGN PATENT DOCUMENTS

| | | |
|---|---|---|
| DE | 4007705 C1 | 9/1991 |
| DE | 4038203 A1 | 6/1992 |
| DE | 4112303 A1 | 10/1992 |
| DE | 4132176 A1 | 4/1993 |
| EP | 0140434 A2 | 5/1985 |
| EP | 0213108 A2 | 3/1987 |
| EP | 0315960 A1 | 5/1989 |
| EP | 0386700 A1 | 9/1990 |
| EP | 0471161 A1 | 2/1992 |
| EP | 0504112 A2 | 9/1992 |
| EP | 0557129 A1 | 8/1993 |
| EP | 0605483 A1 | 7/1994 |
| EP | 0656206 A1 | 6/1995 |
| EP | 0719549 A1 | 7/1996 |
| EP | 1029536 A1 | 8/2000 |
| EP | 2042161 A1 | 4/2009 |
| FR | 2633933 A1 | 1/1990 |
| GB | 2082457 A | 3/1982 |
| GB | 2295318 A | 5/1996 |
| IE | 912509 A1 | 2/1992 |
| JP | 0226661 | 1/1990 |
| WO | WO-90/01046 A1 | 2/1990 |
| WO | WO-93/03751 A1 | 3/1993 |
| WO | WO-93/04671 A1 | 3/1993 |
| WO | WO 9303751 * | 3/1993 |
| WO | WO-94/07514 A1 | 4/1994 |
| WO | WO-94/10987 A1 | 5/1994 |
| WO | WO 9413280 * | 6/1994 |
| WO | WO-95/24893 A1 | 9/1995 |
| WO | WO-95/31217 A1 | 11/1995 |
| WO | WO-97/33621 A1 | 9/1997 |
| WO | WO-97/38662 A2 | 10/1997 |
| WO | WO-97/38663 A2 | 10/1997 |
| WO | WO-97/38687 A1 | 10/1997 |
| WO | WO-97/42938 A1 | 11/1997 |
| WO | WO 9742938 * | 11/1997 |
| WO | WO-98/29097 A1 | 7/1998 |
| WO | WO-98/34595 A1 | 8/1998 |
| WO | WO-98/52540 A1 | 11/1998 |
| WO | WO-98/52545 A1 | 11/1998 |
| WO | WO-99/16417 A1 | 4/1999 |
| WO | WO-99/29097 A1 | 6/1999 |
| WO | WO-00/06534 A1 | 2/2000 |
| WO | WO-00/27359 A1 | 5/2000 |
| WO | WO-00/62757 A1 | 10/2000 |
| WO | WO-01/59142 A1 | 8/2001 |
| WO | WO-01/60420 A1 | 8/2001 |
| WO | WO-01/66089 A2 | 9/2001 |
| WO | WO-01/72338 A1 | 10/2001 |
| WO | WO-02/43695 A2 | 6/2002 |
| WO | WO-02/066089 A2 | 8/2002 |
| WO | WO-02/094232 A1 | 11/2002 |
| WO | WO-02/094234 A1 | 11/2002 |
| WO | WO-2006/089082 A2 | 8/2006 |

OTHER PUBLICATIONS

*Goodman and Gilman's the Pharmacological Basis of Therapeutics*, 9th ed., (1996), pp. 141-154, 169-170, 260, 303-304, 324, 362, 372, 420-422, 427, 471, 472, 478-480, 484, 490, 496-497, 928-930.

Karlsson et al., A comparison of the effect of inhaled diuretics on airway reflexes in humans and guinea pigs, *Am. Physiol. Soc.*, 434-8 (1992).

Mochizuki et al.; Inhaled diuretics attenuate acid-induced cough in children with asthma, *Chest*, 107(2): 413-7 (1995).

(56) References Cited

OTHER PUBLICATIONS

Physician's Desk Reference, pp. 858-861, 2436-2441, 2548-2550 (1995).
Shojaei, Buccal mucosa as a route for systemic drug delivery: A review, *J. Pharmaceut. Sci.* 1(1): 15-30 (1998).
Ting-Chao Chou et al., Pharmacological disposition and metabolic fate of 2'-fluoro-5-iodo-1-8-D-arabinofuranosylcytosine in mice and rats, *Cancer Res.* 41: 3336-42 (1981).

Woodley et al., Manual of Medical Therapeutics, 27th Edition, pp. 341 and 370-371 (1992).
Written Opinion of the International Searching Authority—Feb. 28, 2006.
Ye et al., Ondansetron exhibits the properties of a local anesthetic, *Anesth. Analgesia*, 85(5): 1116-21 (1997).
Zervakis et al.; Taste effects of lingual application of cardiovascular medications, *Physiol. Behav.*, 68: 405-13 (2000).

* cited by examiner

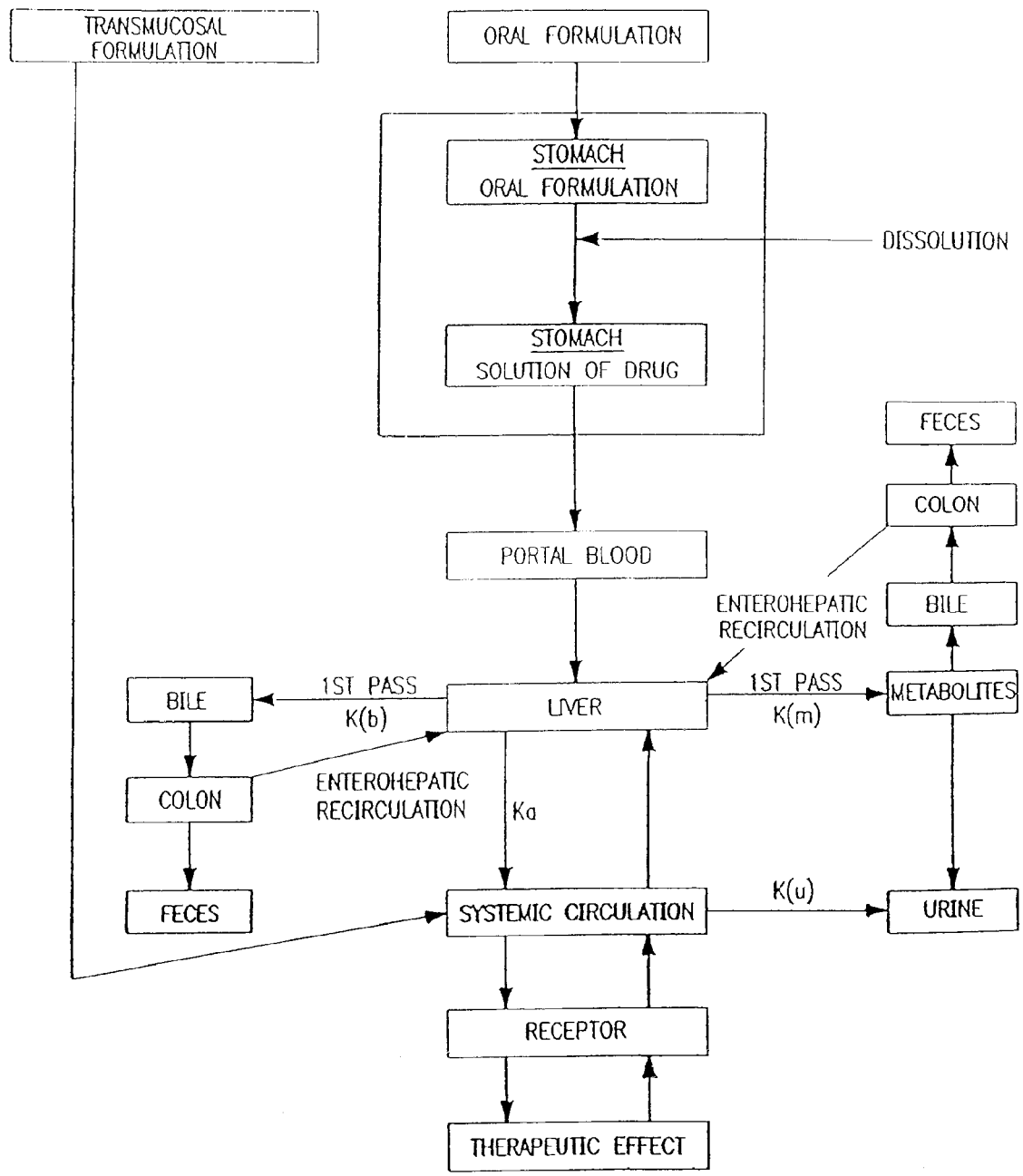

BUCCAL, POLAR AND NON-POLAR SPRAY CONTAINING ONDANSETRON

CROSS REFERENCE TO RELATED APPLICATIONS

The present application is a continuation of Ser. No. 12/350,602 filed Jan. 8, 2009, now abandoned which is a continuation of Ser. No. 11/429,953, which was filed on May 9, 2006, now abandoned, which is a divisional of Ser. No. 10/671,717, which was filed on Sep. 29, 2003 now abandoned, which is a continuation-in-part of application Ser. No. 10/230,085, filed Aug. 29, 2002, now abandoned, which is a continuation-in-part of application Ser. No. 09/537,118, filed Mar. 29, 2000, now abandoned, which is a continuation-in-part of the U.S. national phase designation of PCT/US97/17899, filed Oct. 1, 1997, the disclosures of which are incorporated by reference herein in their entirety.

BACKGROUND OF THE INVENTION

It is known that certain biologically active compounds are better absorbed through the oral mucosa than through other routes of administration, such as through the stomach or intestine. However, formulations suitable for such administration by these latter routes present their own problems. For example, the biologically active compound must be compatible with the other components of the composition such as propellants, solvents, etc. Many such formulations have been proposed. For example, U.S. Pat. No. 4,689,233, Dvorsky et al., describes a soft gelatin capsule for the administration of the anti-coronary drug nifedipine dissolved in a mixture of polyether alcohols. U.S. Pat. No. 4,755,389, Jones et al., describes a hard gelatin chewable capsule containing nifedipine. A chewable gelatin capsule containing a solution or dispersion of a drug is described in U.S. Pat. No. 4,935,243, Borkan et al. U.S. Pat. No. 4,919,919, Aouda et al, and U.S. Pat. No. 5,370,862, Klokkers-Bethke, describe a nitroglycerin spray for administration to the oral mucosa comprising nitroglycerin, ethanol, and other components. An orally administered pump spray is described by Cholcha in U.S. Pat. No. 5,186,925. Aerosol compositions containing a hydrocarbon propellant and a drug for administration to a mucosal surface are described in U.K. 2,082,457, Su, U.S. Pat. No. 3,155,574, Silson et al., U.S. Pat. No. 5,011,678, Wang et al., and by Parnell in U.S. Pat. No. 5,128,132. It should be noted that these references discuss bioavailability of solutions by inhalation rather than through the membranes to which they are administered.

Ondansetron is a 5-HT$_3$ receptor antagonist. The structure of ondansetron is depicted below:

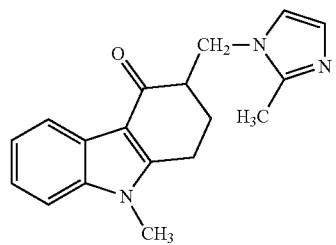 [SMILES: Cc1nccn1CC1CCc2c(c3ccccc3n2C)C1=O]

Ondansetron is an anti-emetic used to treat nausea and/or vomiting, especially chemotherapy and radiation induced nausea and/or vomiting (*Goodman and Gilman's The Pharmacological Basis of Therapeutics*, 9$^{th}$ ed., pp. 260). Ondansetron is also used as a pre-operative anti-emetic (*Goodman and Gilman's The Pharmacological Basis of Therapeutics*, 9$^{th}$ ed., pp. 304). Administration of ondansetron in combination with a corticosteroid, such as phenothiazine or butyrophenone, can increase efficacy as an anti-emetic (*Goodman and Gilman's The Pharmacological Basis of Therapeutics*, 9$^{th}$ ed., pp. 928). Ondansetron can also be used to treat anxiety (*Goodman and Gilman's The Pharmacological Basis of Therapeutics*, 9$^{th}$ ed., pp. 427).

Ondansetron can be administered orally, intravenously, or intramuscularly. Ondansetron, when administered as an anti-emetic for severe chemotherapy-induced emesis, is typically administered at a single daily dose of 32 mg by intravenous infusion over about 15 minutes about 30 minutes prior to chemotherapy or intravenously in 3 divided doses of 0.1 to 0.15 mg/kg with the first dose given about 30 minutes prior to chemotherapy and the following doses given 4 and 8 hours after the initial dose. To treat severe chemotherapy-induced emesis, ondansetron can be administered at a daily dose of 32 mg in combination with a daily dose of 20 mg dexamethasone, each administered by intravenous infusion. For moderate chemotherapy-induced emesis, ondansetron is typically administered orally (as a tablet or solution) at a dose of 8 mg (tablet) or 10 mg (solution) about 30 minutes prior to chemotherapy followed by a second dose 8 hours later. The dose can then be repeated twice per day for 1 to 2 days following chemotherapy (*Goodman and Gilman's The Pharmacological Basis of Therapeutics*, 9$^{th}$ ed., pp. 928-930).

The oral bioavailability of ondansetron is about 60 percent with effective blood levels appearing 30 to 60 minutes after administration. Ondansetron is extensively metabolized by the liver with a plasma half-life of about 3 to 4 hours. Adverse effects of ondansetron are mild and include headaches, constipation, and dizziness (*Goodman and Gilman's The Pharmacological Basis of Therapeutics*, 9$^{th}$ ed., pp. 928-930).

SUMMARY OF THE INVENTION

A buccal aerosol spray or soft bite gelatin capsule using a polar or non-polar solvent has now been developed which provides biologically active compounds for rapid absorption through the oral mucosa, resulting in fast onset of effect.

The buccal aerosol spray compositions of the present invention, for transmucosal administration of a pharmacologically active compound soluble in a pharmacologically acceptable non-polar solvent comprise in weight % of total composition: pharmaceutically acceptable propellant 5-80%, nonpolar solvent 19-85%, active compound 0.05-50%, suitably additionally comprising, by weight of total composition a flavoring agent 0.01-10%. Preferably the composition comprises: propellant 10-70%, non-polar solvent 25-89.9%, active compound 0.01-40%, flavoring agent 1-8%; most suitably propellant 20-70%, non-polar solvent 25-74.75%, active compound 0.25-35%, flavoring agent 2-7.5%.

The buccal polar aerosol spray compositions of the present invention, for transmucosal administration of a pharmacologically active compound soluble in a pharmacologically acceptable polar solvent are also administrable in aerosol form driven by a propellant. In this case, the composition comprises in weight % of total composition: aqueous polar solvent 10-97%, active compound 0.1-25%, suitably additionally comprising, by weight of total composition a flavoring agent 0.05-10% and propellant: 2-10%. Preferably the composition comprises: polar solvent 20-97%, active compound 0.1-15%, flavoring agent 0.1-5% and propellant 2-5%;

most suitably polar solvent 25-97%, active compound 0.2-25%, flavoring agent 0.1-2.5% and propellant 2-4%.

In another embodiment, the buccal polar aerosol spray compositions of the present invention for transmucosal administration of a pharmacologically active compound (i.e., those administrable in aerosol form driven by a propellant) comprises a mixture of a polar solvent and a non-polar solvent comprising in weight % of total composition: solvent 10-97%, active compound 0.05-50%, propellant 5-80%, and optionally a taste mask and/or flavoring agent 0.01-10%. Preferably the composition comprises: solvent 20-97%, active compound 0.1-40%, propellant 10-70%, and taste mask and/or flavoring agent 1-8%; most suitably solvent 25-97%, active compound 0.25-35%, propellant 20-70%, and taste mask and/or flavoring agent 2-7.5%. The ratio of the polar solvent to the non-polar solvent can range from about 1:99 to about 99:1, preferable from about 60:40 to about 40:60, and more preferably about 50:50.

The buccal pump spray composition of the present invention, i.e., the propellant free composition, for transmucosal administration of a pharmacologically active compound wherein said active compound is soluble in a pharmacologically acceptable non-polar solvent comprises in weight % of total composition: non-polar solvent 30-99.69%, active compound 0.005-55%, and suitably additionally, flavoring agent 0.1-10%.

The buccal polar pump spray compositions of the present invention, i.e., the propellant free composition, for transmucosal administration of a pharmacologically active compound soluble in a pharmaceutically acceptable polar solvent comprises in weight % of total composition: aqueous polar solvent 30-99.69%, active compound 0.001-60%, suitably additionally comprising, by weight of total composition a flavoring agent 0.1-10%. Preferably the composition comprises: polar solvent 37-98.58%, active compound 0.005-55%, flavoring agent 0.5-8%; most suitably polar solvent 60.9-97.06%, active compound 0.01-40%, flavoring agent 0.75-7.5%.

In another embodiment, the buccal pump spray composition (i.e., the propellant free composition) for transmucosal administration of a pharmacologically active compound comprises a mixture of a polar solvent and a non-polar solvent comprising in weight % of total composition solvent 30-99.69%, active compound 0.001-60%, and optionally a taste mask and/or flavoring agent 0.1-10%. Preferably the composition comprises: solvent 37-98.58%, active compound 0.005-55%, taste mask and/or flavoring agent 0.5-8%; more preferably the composition comprises solvent 60.9-97.06%, active compound 0.01-40%, and taste mask and/or flavoring agent 0.75-7.5%. The ratio of the polar solvent to the non-polar solvent can range from about 1:99 to about 99:1, preferable about 60:40 to about 40:60, and more preferably about 50:50.

The soft bite gelatin capsules of the present invention for transmucosal administration of a pharmacologically active compound, at least partially soluble in a pharmacologically acceptable non-polar solvent, having charged thereto a fill composition comprise in weight % of total composition: non-polar solvent 4-99.99%, emulsifier 0-20%, active compound 0.01-80%, provided that said fill composition contains less than 10% of water, suitably additionally comprising, by weight of the composition: flavoring agent 0.01-10%. Preferably, the soft bite gelatin capsule comprises: non-polar solvent 21.5-99.975%, emulsifier 0-15%, active compound 0.025-70%, flavoring agent 1-8%; most suitably: nonpolar solvent 28.5-97.9%, emulsifier 0-10%, active compound 0.1-65.0%, flavoring agent 2-6%.

The soft bite polar gelatin capsules of the present invention for transmucosal administration of a pharmacologically active compound, at least partially soluble in a pharmacologically acceptable polar solvent, having charged thereto a composition comprising in weight % of total composition: polar solvent 25-99.89%, emulsifier 0-20%, active compound 0.01-65%, provided that said composition contains less than 10% of water, suitably additionally comprising, by weight of the composition: flavoring agent 01-10%. Preferably, the soft bite gelatin capsule comprises: polar solvent 37-99.95%, emulsifier 0-15%, active compound 0.025-55%, flavoring agent 1-8%; most suitably: polar solvent 44-96.925%, emulsifier 0-10%, active compound 0.075-50%, flavoring agent 2-6%.

It is an object of the invention to coat the mucosal membranes either with extremely fine droplets of spray containing the active compounds or a solution or paste thereof from bite capsules.

It is also an object of the invention to administer to the oral mucosa of a mammalian in need of same, preferably man, by spray or bite capsule, a predetermined amount of a biologically active compound by this method or from a soft gelatin capsule.

A further object is a sealed aerosol spray container containing a composition of the non polar or polar aerosol spray formulation, and a metered valve suitable for releasing from said container a predetermined amount of said composition.

As the propellant evaporates after activation of the aerosol valve, a mist of fine droplets is formed which contains solvent and active compound.

The propellant is a non-Freon material, preferably a $C_{3-8}$ hydrocarbon of a linear or branched configuration. The propellant should be substantially non-aqueous. The propellant produces a pressure in the aerosol container such that under expected normal usage it will produce sufficient pressure to expel the solvent from the container when the valve is activated but not excessive pressure such as to damage the container or valve seals.

The non-polar solvent is a non-polar hydrocarbon, preferably a $C_{7-18}$ hydrocarbon of a linear or branched configuration, fatty acid esters, and triglycerides, such as MIGLYOL®. The solvent must dissolve the active compound and be miscible with the propellant, i.e., solvent and propellant must form a single phase at a temperature of 0-40° C. a pressure range of between 1-3 atm.

The polar and non-polar aerosol spray compositions of the invention are intended to be administered from a sealed, pressurized container. Unlike a pump spray, which allows the entry of air into the container after every activation, the aerosol container of the invention is sealed at the time of manufacture. The contents of the container are released by activation of a metered valve, which does not allow entry of atmospheric gasses with each activation. Such containers are commercially available.

A further object is a pump spray container containing a composition of the pump spray formulation, and a metered valve suitable for releasing from said container a predetermined amount of said composition.

A further object is a soft gelatin bite capsule containing a composition of as set forth above. The formulation may be in the form of a viscous solution or paste containing the active compounds. Although solutions are preferred, paste fills may also be used where the active compound is not soluble or only partially soluble in the solvent of choice. Where water is used to form part of the paste composition, it should not exceed 10% thereof. (All percentages herein are by weight unless otherwise indicated.)

The polar or non-polar solvent is chosen such that it is compatible with the gelatin shell and the active compound. The solvent preferably dissolves the active compound. However, other components wherein the active compound is not soluble or only slightly soluble may be used and will form a paste fill.

Soft gelatin capsules are well known in the art. See, for example, U.S. Pat. No. 4,935,243, Borkan et al., for its teaching of such capsules. The capsules of the present invention are intended to be bitten into to release the low viscosity solution or paste therein, which will then coat the buccal mucosa with the active compounds. Typical capsules, which are swallowed whole or bitten and then swallowed, deliver the active compounds to the stomach, which results in significant lag time before maximum blood levels can be achieved or subject the compound to a large first pass effect. Because of the enhanced absorption of the compounds through the oral mucosa and no chance of a first pass effect, use of the bite capsules of the invention will eliminate much of the lag time, resulting in hastened onset of biological effect. The shell of a soft gelatin capsule of the invention may comprise, for example: gelatin: 50-75%, glycerin 20-30%, colorants 0.5-1.5%, water 5-10%, and sorbitol 2-10%.

The active compound may include, biologically active peptides, central nervous system active amines, sulfonyl ureas, antibiotics, antifungals, antivirals, sleep inducers, antiasthmatics, bronchial dilators, antiemetics, histamine H-2 receptor antagonists, barbiturates, prostaglandins and neutraceuticals.

The active compounds may also include antihistamines, alkaloids, hormones, benzodiazepines and narcotic analgesics. While not limited thereto, these active compounds are particularly suitable for non-polar pump spray formulation and application.

The active compounds may also include anti-diuretics, anti-muscle spasm agents, anti-spasmodics, agents for treating urinary incontinence, anti-diarrheal agents, agents for treating nausea and/or vomiting, smooth muscle contractile agents, anti-secretory agents, enzymes, anti-diuretics, anti-ulcerants, bile acid replacement and/or gallstone solubilizing drugs, or mixtures thereof.

In one embodiment, the active compound is ondansetron or a pharmaceutically acceptable salt thereof.

BRIEF DESCRIPTION OF THE DRAWING

FIG. 1. is a schematic diagram showing routes of absorption and processing of pharmacologically active substances in a mammalian system.

DESCRIPTION OF THE PREFERRED EMBODIMENTS

The preferred active compounds of the present invention are in an ionized, salt form or as the free base of the pharmaceutically acceptable salts thereof (provided, for the aerosol or pump spray compositions, they are soluble in the spray solvent). These compounds are soluble in the non-polar solvents of the invention at useful concentrations or can be prepared as pastes at useful concentrations. These concentrations may be less than the standard accepted dose for these compounds since there is enhanced absorption of the compounds through the oral mucosa. This aspect of the invention is especially important when there is a large (40-99.99%) first pass effect.

As propellants for the non polar sprays, propane, N-butane, iso-butane, N-pentane, iso-pentane, and neo-pentane, and mixtures thereof may be used. N-butane and iso-butane, as single gases, are the preferred propellants. It is permissible for the propellant to have a water content of no more than 0.2%, typically 0.1-0.2%. All percentages herein are by weight unless otherwise indicated. It is also preferable that the propellant be synthetically produced to minimize the presence of contaminants which are harmful to the active compounds. These contaminants include oxidizing agents, reducing agents, Lewis acids or bases, and water. The concentration of each of these should be less than 0.1%, except that water may be as high as 0.2%.

Suitable non-polar solvents for the capsules and the non-polar sprays include ($C_2$-$C_{24}$) fatty acid ($C_2$-$C_6$) esters, $C_7$-$C_{18}$ hydrocarbon, $C_2$-$C_6$ alkanoyl esters, and the triglycerides of the corresponding acids. When the capsule fill is a paste, other liquid components may be used instead of the above low molecular weight solvents. These include soya oil, corn oil, other vegetable oils.

As solvents for the polar capsules or sprays there may be used low molecular weight polyethyleneglycols (PEG) of 400-1000 Mw (preferably 400-600), low molecular weight ($C_2$-$C_8$) mono and polyols and alcohols of C $C_7$-$C_{18}$ linear or branch chain hydrocarbons, glycerin may also be present and water may also be used in the sprays, but only in limited amount in the capsules.

It is expected that some glycerin and water used to make the gelatin shell will migrate from the shell to the fill during the curing of the shell. Likewise, there may be some migration of components from the fill to the shell during curing and even throughout the shelf-life of the capsule.

Therefore, the values given herein are for the compositions as prepared, it being within the scope of the invention that minor variations will occur.

The preferred flavoring agents are synthetic or natural oil of peppermint, oil of spearmint, citrus oil, fruit flavors, sweeteners (sugars, aspartame, saccharin, etc.), and combinations thereof.

The compositions may further include a taste mask. The term "taste mask" as used herein means an agent that can hide or minimize an undesirable flavor such as a bitter or sour flavor. A representative taste mask is a combination of vanillin, ethyl vanillin, maltol, iso-amyl acetate, ethyl oxyhydrate, anisic aldehyde, and propylene glycol (commercially available as "PFC 9885 Bitter Mask" from Pharmaceutical Flavor Clinic of Camden, N.J.). A taste mask in combination with a flavoring agent is particularly advantageous when the active compound is an alkaloid since alkaloids often have a bitter taste.

The active substances include the active compounds selected from the group consisting of cyclosporine, sermorelin, octreotide acetate, calcitonin-salmon, insulin lispro, sumatriptan succinate, clozapine, cyclobenzaprine, dexfenfluramine hydrochloride, glyburide, zidovudine, erythromycin, ciprofloxacin, ondansetron hydrochloride, dimenhydrinate, cimetidine hydrochloride, famotidine, phenyloin sodium, phenyloin, carboprost tromethamine, carboprost, diphenhydramine hydrochloride, isoproterenol hydrochloride, terbutaline sulfate, terbutaline, theophylline, albuterol sulfate and neutraceuticals, that is to say nutrients with pharmacological action such as but not limited to carnitine, valerian, echinacea, and the like.

In another embodiment, the active compound is an anti-diuretic, anti-muscle spasm agent, anti-spasmodic, agent for treating urinary incontinence, anti-diarrheal agent, agent for treating nausea and/or vomiting, smooth muscle contractile agent, anti-secretory agent, enzyme, anti-diuretic, anti-ulcerant, bile acid replacement and/or gallstone solubilizing drug, or a mixture thereof.

In one embodiment the active compound is an anti-diuretic. Suitable anti-diuretics for use in the buccal sprays of the invention include, but are not limited to, acetazolamide, benzthiazide, bendroflumethazide, bumetanide, chlorthalidone, chlorothiazide, ethacrynic acid, furosemide, hydrochlorothiazide, hydroflumethiazide, methyclothiazide, polythiazide, quinethazone, spironolactone, triamterene, torsemide, trichlomethiazide, and mixtures thereof.

In one embodiment the active compound is an anti-muscle spasm agent. Suitable anti-muscle spasm agents for use in the buccal sprays of the invention include, but are not limited to, baclofen, botulinum toxin, carisoprodol, chlorphenesin, chlorzoxazone, cyclobenzaprine, dantrolene, diazepam, metaxalone, methocarbamol, orphenadrine, tizanidine, and mixtures thereof.

In one embodiment the active compound is an anti-spasmodic. Suitable anti-spasmodics for use in the buccal sprays of the invention include, but are not limited to, atropine, baclofen, dicyclomine, hyoscine, propatheline, oxybutynin, S-oxybutynin, tizanidine, and mixtures thereof.

In one embodiment the active compound is an agent for treating urinary incontinence. Suitable agents for treating urinary incontinence for use in the buccal sprays of the invention include, but are not limited to, darifenacin, vamicamide, detrol, ditropan, imipramine, and mixtures thereof.

In one embodiment the active compound is an anti-diarrheal agent. Suitable anti-diarrheal agents for use in the buccal sprays of the invention include, but are not limited to, ondansetron, palnosetron, tropisetron, attapulgite, atropine, bismuth, diphenoxylate, loperamide, and mixtures thereof.

In one embodiment the active compound is an agent for treating nausea and/or vomiting. Suitable agents for treating nausea and/or vomiting for use in the buccal sprays of the invention include, but are not limited to, alosetron, dolasetron, granisetron, meclizine, metoclopramide, ondansetron, palnosetron, prochloperazine, promethazine, trimethobenzamiode, tropisetron, and mixtures thereof.

In one embodiment the active compound is a smooth muscle contractile agent. A suitable smooth muscle contractile agents for use in the buccal sprays of the invention includes, but is not limited to hyoscine.

In one embodiment the active compound is an anti-secretory agent. Suitable anti-secretory agents for use in the buccal sprays of the invention include, but are not limited to, esomeprazole, lansoprazole, omeprazole, pantoprazole, rabeprazole, tenetoprazole, ecabet, misoprostol, teprenone, and mixtures thereof.

In one embodiment the active compound is an enzyme. Suitable enzymes for use in the buccal sprays of the invention include, but are not limited to, alpha-galactosidase, alpha-L-iduronidase, imiglucerase/alglucerase, amylase, lipase, protease, pancreatin, olsalazine, and mixtures thereof.

In one embodiment the active compound is an anti-diuretic. Suitable anti-diuretics for use in the buccal sprays of the invention include, but are not limited to, desmopressin, oxytocin, and mixtures thereof.

In one embodiment the active compound is an anti-ulcerant. Suitable anti-ulcerants for use in the buccal sprays of the invention include, but are not limited to, cimetidine, ranitidine, famotidine, misoprostol, sucralfate, pantoprazole, lansoprazole, omeprazole, and mixtures thereof.

In one embodiment the active compound is a bile acid replacement and/or gallstone solubilizing drug. A suitable bile acid replacement and/or gallstone solubilizing drug for use in the buccal sprays of the invention includes, but is not limited to ursodiol.

In one embodiment, the active compound is ondansetron, or a pharmaceutically acceptable salt thereof. In one embodiment, the active compound is ondansetron hydrochloride.

Typically, when ondansetron, or a pharmaceutically acceptable salt thereof, is the active compound the buccal spray contains from about contains form about 0.01 to 20 weight/weight (w/w) percent ondansetron, or a pharmaceutically acceptable salt thereof, preferably, about 0.1 to 15 w/w percent, and more preferably about 0.2 to 10 w/w percent ondansetron, or a pharmaceutically acceptable salt thereof.

The invention further relates to a method for treating emesis in a patient by spraying the oral mucosa of the patient with a therapeutically effective amount of a buccal spray comprising ondansetron or a pharmaceutically acceptable salt thereof.

In one embodiment, the emesis is chemotherapy induced emesis.

In another embodiment, the emesis is radiation induced emesis.

In another embodiment, the ondansetron, or a pharmaceutically acceptable salt thereof, is administered in combination with a corticosteroid, such as phenothiazine or butyrophenone.

In another embodiment, the ondansetron, or a pharmaceutically acceptable salt thereof, is administered in combination with dexamethasone.

In another embodiment for treating chemotherapy or radiation induced emesis, the oral mucosa of the patient is sprayed with ondansetron, or a pharmaceutically acceptable salt thereof, before chemotherapy or radiation therapy begins. Typically, ondansetron, or a pharmaceutically acceptable salt thereof, is sprayed on the oral mucosa of the patient between about 5 minutes and about 2 hours before chemotherapy or radiation therapy begins, preferably between about 15 minutes and about 1 hour, more preferably between about 30 minutes before chemotherapy or radiation therapy begins. In another embodiment, the method further includes administering ondansetron, or a pharmaceutically acceptable salt thereof, after chemotherapy or radiation therapy is ended. Typically, the ondansetron, or a pharmaceutically acceptable salt thereof, is sprayed on the oral mucosa of the patient between about 1 hour and 6 hours after chemotherapy or radiation therapy has ended, preferable between about 2 hours and about 5 hours, more preferably about 4 hours after chemotherapy or radiation therapy has ended.

In another embodiment, the emesis is anesthetic induced emesis. Accordingly, the invention further relates to a method of administering anesthesia by spraying the oral mucosa of the patient with a therapeutically effective amount of a buccal spray comprising ondansetron or a pharmaceutically acceptable salt thereof before the anesthesis is administered.

The invention further relates to a method for treating anxiety in a patient by spraying the oral mucosa of the patient with a therapeutically effective amount of a buccal spray comprising ondansetron or a pharmaceutically acceptable salt thereof.

The formulations of the present invention comprise an active compound or a pharmaceutically acceptable salt thereof. The term "pharmaceutically acceptable salts" refers to salts prepared from pharmaceutically acceptable non-toxic acids or bases including organic and inorganic acids or bases.

When an active compound of the present invention is acidic, salts may be prepared from pharmaceutically acceptable non-toxic bases. Salts derived from all stable forms of inorganic bases include aluminum, ammonium, calcium, copper, iron, lithium, magnesium, manganese, potassium, sodium, zinc, etc. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion-exchange resins such as arginine, betaine, caffeine, choline, N,N dibenzylethylenediamine, diethylamine, 2-diethylaminoethanol, 2-dimethylaminoethanol, ethanolamine, ethylenediamine, N-ethylnorpholine, N-ethylpiperidine, glucamine, glucosamine, histidine, isopropylamine, lysine, methyl-glucosamine, morpholine, piperazine, piperidine, polyamine resins, procaine, purine, theobromine, triethylamine, trimethylamine, tripropylamine, etc.

When an active compound of the present invention is basic, salts may be prepared from pharmaceutically acceptable non-toxic acids. Such acids include acetic, benzenesulfonic, benzoic, camphorsulfonic, citric, ethane-sulfonic, fumaric, gluconic, glutamic, hydrobromic, hydrochloric, isethionic, lactic, maleic, mandelic, methanesulfonic, mucic, nitric, pamoic, pantothenic, phosphoric, succinic, sulfuric, tartaric, p-toluenesulfonic, etc. Particularly preferred are citric, hydrobromic, maleic, phosphoric, sulfuric, and tartaric acids.

In the discussion of methods of treatment herein, reference to the active compounds is meant to also include the pharmaceutically acceptable salts thereof. While certain formulations are set forth herein, the actual amounts to be administered to the mammal or man in need of same are to be determined by the treating physician.

The invention is further defined by reference to the following examples, which are intended to be illustrative and not limiting.

The following are examples of certain classes. All values unless otherwise specified are in weight percent.

EXAMPLES

Example 1

Biologically Active Peptides Including Peptide Hormones

A. Cyclosporine Lingual Spray

|  | Amount | Preferred Amount | Most-Preferred Amount |
| --- | --- | --- | --- |
| cyclosporine | 5-50 | 10-35 | 15-25 |
| water | 5-20 | 7.5-50 | 9.5-12 |
| ethanol | 5-60 | 7.5-50 | 10-20 |
| polyethylene glycol | 20-60 | 30-45 | 35-40 |
| flavors | 0.1-5 | 1-4 | 2-3 |

B. Cyclosporine Non-Polar Lingual Spray

|  | Amounts | preferred amount | most preferred amount |
| --- | --- | --- | --- |
| cyclosporine | 1-50 | 3-40 | 5-30 |
| MIGLYOL ® | 20 | 25 | 30-40 |
| Polyoxyethylated castor oil | 20 | 25 | 30-40 |
| Butane | 25-80 | 30-70 | 33-50 |
| flavors | 0.1-5 | 1-4 | 2-3 |

C. Cyclosporine Non-Polar Bite Capsule

|  | Amounts | preferred amount | most preferred amount |
| --- | --- | --- | --- |
| cyclosporine | 1-35 | 5-25 | 10-20 |
| olive oil | 25-60 | 35-55 | 30-45 |
| polyoxyethylated oleic glycerides | 25-60 | 35-55 | 30-45 |
| flavors | 0.1-5 | 1-4 | 2-3 |

D. Cyclosporine Bite Capsule

|  | Amount | Preferred Amount | Most-Preferred Amount |
| --- | --- | --- | --- |
| cyclosporine | 5-50 | 10-35 | 15-25 |
| polyethylene | 20-60 | 30-45 | 35-40 |
| glycol glycerin | 5-30 | 7.5-25 | 10-20 |
| propylene glycol | 5-30 | 7.5-25 | 10-20 |
| flavors | 0.1-10 | 1-8 | 3-6 |

E. Sermorelin (as the Acetate) Lingual Spray

|  | Amount | Preferred Amount | Most-Preferred Amount |
| --- | --- | --- | --- |
| sermorelin (as the acetate) | .01-5 | .1-3 | .2-1.0 |
| mannitol | 1-25 | 5-20 | 10-15 |
| monobasic sodium phosphate, | 0.1-5 | 1-31 | .5-2.5 |
| dibasic sodium phosphate water | 0.01-5 | .05-3 | 0.1-0.5 |
| ethanol | 5-30 | 7.5-25 | 9.5-15 |
| polyethylene glycol | 20-60 | 30-45 | 35-40 |
| propylene glycol | 5-25 | 10-20 | 12-17 |
| flavors | 0.1-5 | 1-4 | 2-3 |

F. Octreotide Acetate (Sandostatin) Lingual Spray

|  | Amounts | preferred amount | most preferred amount |
| --- | --- | --- | --- |
| octreotide acetate | 0.001-0.5 | 0.005-0.250 | 0.01-0.10 |
| acetic acid | 1-10 | 2-8 | 4-6 |
| sodium acetate | 1-10 | 2-8 | 4-6 |
| sodium chloride | 3-30 | .5-25 | 15-20 |
| ethanol | 5-30 | 7.5-20 | 9.5-15 |
| water | 15-95 | 35-90 | 65-85 |
| flavors | 0.1-5 | 1-4 | 2-3 |

G. Calcitonin-Salmon Lingual Spray

|  | Amount | Preferred Amount | Most-Preferred Amount |
| --- | --- | --- | --- |
| calcitonin-salmon | 0.001-5 | 0.005-2 | 01-1.5 |
| ethanol | 2-15 | 3-10 | 7-9.5 |
| water | 30-95 | 50-90 | 60-80 |
| polyethylene | 2-15 | 3-10 | 7-9.5 |
| glycol sodium chloride | 2.5-20 | 5-15 | 10-12.5 |
| flavors | 0.1-5 | 1-4 | 2-3 |

H. Insulin Lispro, Lingual Spray

|  | Amount | Preferred Amount | Most-Preferred Amount |
| --- | --- | --- | --- |
| insulin | 20-60 | 4-55 | 5-50 |
| glycerin | 0.1-10 | 0.25-5 | 0.1-1.5 |

-continued

|  | Amount | Preferred Amount | Most-Preferred Amount |
|---|---|---|---|
| dibasic sodium phosphate | 1-15 | 2.5-10 | 4-8 |
| m-cresol, | 1-25 | 5-25 | 7.5-12.5 |
| zinc oxide | 0.01-0.25 | .05-0.15 | 0.075-0.10 |
| m-cresol | 0.1-1 | 0.2-0.8 | 0.4-0.6 |
| phenol | trace amounts | trace amounts | trace amounts |
| ethanol | 5-20 | 7.5-15 | 9-12 |
| water | 30-90 | 40-80 | 50-75 |
| propylene glycol | 5-20 | 7.5-15 | 9-12 |
| flavors | 0.1-5 | 0.5-3 | 0.75-2 | adjust pH to 7.0-7.8 with HCl or NaOH

Example 2

CNS Active Amines and their Salts: Including but not Limited to Tricyclic Amines, GABA Analogues, Thiazides, Phenothiazine Derivatives, Serotonin Antagonists and Serotonin Reuptake Inhibitors A. Sumatriptan Succinate Lingual Spray

|  | Amount | Preferred Amount | Most-Preferred Amount |
|---|---|---|---|
| sumatriptan succinate | 0.5-30 | 1-20 | 10-15 |
| ethanol | 5-60 | 7.5-50 | 10-20 |
| propylene glycol | 5-30 | 7.5-20 | 10-15 |
| polyethylene glycol | 0-60 | 30-45 | 35-40 |
| water | 5-30 | 7.5-20 | 10-15 |
| flavors | 0.1-5 | 1-4 | 2-3 |

B. Sumatriptan Succinate Bite Capsule

|  | Amount | Preferred Amount | Most-Preferred Amount |
|---|---|---|---|
| sumatriptan succinate | 0.01-5 | 0.05-3.5 | 0.075-1.75 |
| polyethylene glycol | 25-70 | 30-60 | 35-50 |
| glycerin | 25-70 | 30-60 | 35-50 |
| flavors | 0.1-10 | 1-8 | 3-6 |

C. Clozapine Lingual Spray

|  | Amounts | preferred amount | most preferred amount |
|---|---|---|---|
| clozapine | 0.5-30 | 1-20 | 10-15 |
| ethanol | 5-60 | 7.5-50 | 10-20 |
| propylene glycol | 5-30 | 7.5-20 | 10-15 |
| polyethylene glycol | 0-60 | 30-45 | 35-40 |
| water | 5-30 | 7.5-20 | 10-15 |
| flavors | 0.1-5 | 1-4 | 2-3 |

D. Clozapine Non-Polar Lingual Spray with Propellant

|  | Amounts | preferred amount | most preferred amount |
|---|---|---|---|
| clozapine | 0.5-30 | 1-20 | 10-15 |
| MIGLYOL ® | 20-85 | 25-70 | 30-40 |
| Butanol | 5-80 | 30-75 | 60-70 |
| flavors | 0.1-5 | 1-4 | 2-3 |

E. Clozapine Non-Polar Lingual Spray without Propellant

|  | Amounts | preferred amount | most preferred amount |
|---|---|---|---|
| clozapine | 0.5-30 | 1-20 | 10-15 |
| MIGLYOL ® | 70-99.5 | 80-99 | 85-90 |
| flavors | 0.1-5 | 1-4 | 2-3 |

F. Cyclobenzaprine Non-Polar Lingual Spray

|  | Amounts | preferred amount | most preferred amount |
|---|---|---|---|
| cyclobenzaprine (base) | 0.5-30 | 1-20 | 10-15 |
| MIGLYOL ® | 20-85 | 25-70 | 30-40 |
| Iso-butane | 15-80 | 30-75 | 60-70 |
| flavors | 0.1-5 | 1-4 | 2-3 |

G. Dexfenfluramine Hydrochloride Lingual Spray

|  | Amounts | preferred amount | most preferred amount |
|---|---|---|---|
| dexfenfluramine HCl | 5-30 | 7.5-20 | 10-15 |
| ethanol | 5-60 | 7.5-50 | 10-20 |
| propylene glycol | 5-30 | 7.5-20 | 10-15 |
| polyethylene glycol | 0-60 | 30-45 | 35-40 |
| water | 5-30 | 7.5-20 | 10-15 |
| flavors | 0.1-5 | 1-4 | 2-3 |

Example 3

Sulfonylureas

A. Glyburide Lingual Spray

|  | Amounts | preferred amount | most preferred amount |
|---|---|---|---|
| glyburide | 0.25-25 | 0.5-20 | 0.75-15 |
| ethanol | 5-60 | 7.5-50 | 10-20 |
| propylene glycol | 5-30 | 7.5-20 | 10-15 |
| polyethylene glycol | 0-60 | 30-45 | 35-40 |
| water | 2.5-30 | 5-20 | 6-15 |
| flavors | 0.1-5 | 1-4 | 2-3 |

B. Glyburide Non-Polar Bite Capsule

|  | Amount | Preferred Amount | Most-Preferred Amount |
|---|---|---|---|
| glyburide | 0.01-10 | 0.025-7.5 | 0.1-4 |
| olive oil | 30-60 | 35-55 | 30-50 |
| polyoxyethylated oleic glycerides | 30-60 | 35-55 | 30-50 |
| flavors | 0.1-5 | 1-4 | 2-3 |

Example 4

Antibiotics Anti-Fungals and Anti-Virals

A. Zidovudine [Formerly Called Azidothymidine (AZT) (Retrovir)] Non-Polar Lingual Spray

|  | Amount | Preferred Amount | Most-Preferred Amount |
| --- | --- | --- | --- |
| zidovudine | 0-50 | 15-40 | 25-35 |
| Soya oil | 20-85 | 25-70 | 30-40 |
| Butane | 15-80 | 30-75 | 60-70 |
| flavors | 0.1-5 | 1-4 | 2-3 |

B. Erythromycin Bite Capsule

|  | Amounts | preferred amount | most preferred amount |
| --- | --- | --- | --- |
| erythromycin | 25-65 | 30-50 | 35-45 |
| polyoxyethylene glycol | 5-70 | 30-60 | 45-55 |
| glycerin | 5-20 | 7.5-15 | 10-12.5 |
| flavors | 1-10 | 2-8 | 3-6 |

C. Iprofloxacin Hydrochloride Bite Capsule

|  | Amount | Preferred Amount | Most-Preferred Amount |
| --- | --- | --- | --- |
| ciprofloxacin hydrochloride | 25-65 | 35-55 | 40-50 |
| glycerin | 5-20 | 7.5-15 | 10-12.5 |
| polyethylene glycol | 120-75 | 30-65 | 40-60 |
| flavors | 1-10 | 2-8 | 3-6 |

D. Idovudine [Formerly Called Azidothymidine (AZT) (Retrovir)] Lingual Spray

|  | Amount | Preferred Amount | Most-Preferred Amount |
| --- | --- | --- | --- |
| zidovudine | 10-50 | 15-40 | 25-35 |
| water | 30-80 | 40-75 | 45-70 |
| ethanol | 5-20 | 7.5-15 | 9.5-12.5 |
| polyethylene glycol | 5-20 | 7.5-15 | 9.5-12.5 |
| flavors | 0.1-5 | 1-4 | 2-3 |

Example 5

Anti-Emetics

A. Ondansetron Hydrochloride Lingual Spray

|  | Amount | Preferred Amount | Most-Preferred Amount |
| --- | --- | --- | --- |
| ondansetron hydrochloride | 1-25 | 2-20 | 2.5-15 |
| citric acid monohydrate | 1-10 | 2-8 | 2.5-5 |
| sodium citrate dihydrate | 0.5-5 | 1-4 | 1.25-2.5 |
| water | 1-90 | 5-85 | 10-75 |
| ethanol | 5-30 | 7.5-20 | 9.5-15 |
| propylene glycol | 5-30 | 7.5-20 | 9.5-15 |
| polyethylene glycol | 5-30 | 7.5-20 | 9.5-15 |
| flavors | 1-10 | 3-8 | 5-7.5 |

B. A Propellant Free Ondansetron Formulation in a Polar Solvent can be Made According to the Following Formula:

| Component | Percent (w/w) |
| --- | --- |
| Ondansetron Hydrochloride | 4 |
| Tween 80 | 0.5 |
| EDTA | 0.02 |
| Ethanol | 10 |
| Glycerol | 5 |
| Water | QS to 100 |

C. A Propellant Free Ondansetron Formulation in a Non-Polar Solvent can be Made According to the Following Formula

| Component | Percent (w/w) |
| --- | --- |
| Ondansetron | 0.2 |
| Bitter Mask | 0.50.1 |
| Alpha-tocopherol Acetate | 2 |
| Liquid Paraffin | QS to 100 |

D. A Propellant Free Ondansetron Formulation in a Mixture of a Polar Solvent and a Non-Polar Solvent can be Made According to the Following Formula

| Component | Percent (w/w) |
| --- | --- |
| Ondansetron | 0.1 |
| MIGLYOL ® 810 | 20 |
| Polysorbate (span) | 1 |
| Lemon oil | 0.1 |
| Ethanol | QS to 100 |

E. An Ondansetron Formulation in a Non-Polar Solvent with a Propellant can be Made According to the Following Formula:

| Component | Percent (w/w) |
| --- | --- |
| Ondansetron | 0.1 |
| Lemon oil | 0.2 |
| MIGLYOL ® | 20 |
| Butane | QS to 100 |

F. An Ondansetron Formulation in a Polar Solvent with a Propellant can be Made According to the Following Formula:

| Component | Percent (w/w) |
| --- | --- |
| Ondansetron | 2 |
| Bitter mask | 0.2 |
| Ethanol | 60 |
| Butane | 100 |

G. An Ondansetron Formulation in a Mixture of a Polar Solvent and a Non-Polar Solvent with a Propellant can be Made According to the Following Formula:

| Component | Percent (w/w) |
| --- | --- |
| Ondansetron | 0.1 |
| MIGLYOL ® 810 | 20 |
| Polysorbate (span) | 1 |

-continued

| Component | Percent (w/w) |
|---|---|
| Lemon oil | 0.1 |
| Ethanol | 20 |
| Butane | QS to 100 |

H. Dimenhydrinate Bite Capsule

| | Amount | Preferred Amount | Most-Preferred Amount |
|---|---|---|---|
| dimenhydrinate | 0.5-30 | 2-25 | 3-15 |
| glycerin | 5-20 | 7.5-15 | 10-12.5 |
| polyethylene glycol | 45-95 | 50-90 | 55-85 |
| flavors | 1-10 | 2-8 | 3-6 |

I. Dimenhydrinate Polar Lingual Spray

| | Amount | Preferred Amount | Most-Preferred Amount |
|---|---|---|---|
| dimenhydrinate | 3-50 | 4-40 | 5-35 |
| water | 5-90 | 10-80 | 15-75 |
| ethanol | 1-80 | 3-50 | 5-10 |
| polyethylene glycol | 1-80 | 3-50 | 5-15 |
| sorbitol | 0.1-5 | 0.2-40 | 0.4-1.0 |
| aspartame | 0.01-0.5 | 0.02-0.4 | 0.04-0.1 |
| flavors | 0.1-5 | 1-4 | 2-3 |

Example 6

Histamine H-2 Receptor Antagonists

A. Cimetidine Hydrochloride Bite Capsule

| | Amount | Preferred Amount | Most-Preferred Amount |
|---|---|---|---|
| cimetidine HCl | 10-60 | 15-55 | 25-50 |
| glycerin | 5-20 | 7.5-15 | 10-12.5 |
| polyethylene glycol | 20-90 | 25-85 | 30-75 |
| flavors | 1-10 | 2-8 | 3-6 |

B. Famotidine Lingual Spray

| | Amount | Preferred Amount | Most-Preferred Amount |
|---|---|---|---|
| famotidine | 1-35 | 5-30 | 7-20 |
| water | 2.5-25 | 3-20 | 5-10 |
| L-aspartic acid | 0.1-20 | 1-15 | 5-10 |
| polyethylene glycol | 20-97 | 30-95 | 50-85 |
| flavors | 0.1-10 | 1-7.5 | 2-5 |

C. Famotidine Non-Polar Lingual Spray

| | Amounts | preferred amount | most preferred amount |
|---|---|---|---|
| famotidine | 1-35 | 5-30 | 7-20 |
| Soya oil | 10-50 | 15-40 | 15-20 |
| Butanol | 5-80 | 30-75 | 45-70 |
| polyoxyethylated oleic glycerides | 10-50 | 15-40 | 15-20 |
| flavors | 0.1-5 | 1-4 | 2-3 |

Example 7

Barbiturates

A. Phenyloin Sodium Lingual Spray

| | Amount | Preferred Amount | Most-Preferred Amount |
|---|---|---|---|
| phenytoin sodium | 10-60 | 15-55 | 20-40 |
| water | 2.5-25 | 3-20 | 5-10 |
| ethanol | 5-30 | 7.5-20 | 9.5-15 |
| propylene glycol | 5-30 | 7.5-20 | 9.5-15 |
| polyethylene glycol | 5-30 | 7.5-20 | 9.5-15 |
| flavors | 1-10 | 3-8 | 5-7.5 |

B. Phenyloin Non-Polar Lingual Spray

| | Amounts | preferred amount | most preferred amount |
|---|---|---|---|
| phenytoin | 5-45 | 10-40 | 15-35 |
| MIGLYOL ® | 10-50 | 15-40 | 15-20 |
| Butane | 15-80 | 30-75 | 60-70 |
| polyoxyethylated oleic glycerides | 10-50 | 15-40 | 15-20 |
| flavors | 0.1-10 | 1-8 | 5-7.5 |

Example 8

Prostaglandins

A. Carboprost Tromethamine Lingual Spray

| | Amounts | preferred amount | most preferred amount |
|---|---|---|---|
| carboprost tromethamine | 0.05-5 | 0.1-3 | 0.25-2.5 |
| water | 50-95 | 60-80 | 65-75 |
| ethanol | 5-20 | 7.5-15 | 9.5-12.5 |
| polyethylene glycol | 5-20 | 7.5-15 | 9.5-12.5 |
| sodium chloride | 1-20 | 3-15 | 4-8 |
| flavors | 0.1-5 | 1-4 | 2-3 | pH is adjusted with sodium hydroxide and/or hydrochloric acid

B. Carboprost Non-Polar Lingual Spray

| | Amounts | preferred amount | most preferred amount |
|---|---|---|---|
| carboprost | 0.05-5 | 0.1-3 | 0.25-2.5 |
| MIGLYOL ® | 25-50 | 30-45 | 35-40 |
| Butane | 5-60 | 10-50 | 20-35 |
| polyoxyethylated oleic glycerides | 25-50 | 30-45 | 35-40 |
| flavors | 0.1-10 | 1-8 | 5-7.5 |

Example 9

Neutraceuticals

A. Carnitine as Bite Capsule (Contents are a Paste)

| | Amount | Preferred Amount | Most-Preferred Amount |
|---|---|---|---|
| carnitine fumarate | 6-80 | 30-70 | 45-65 |
| soya oil | 7.5-50 | 10-40 | 12.5-35 |
| soya lecithin | 0.001-1.0 | 0.005-0.5 | .01-0.1 |
| Soya fats | 7.5-50 | 10-40 | 12.5-35 |
| flavors | 1-10 | 2-8 | 3-6 |

B. Valerian as Lingual Spray

| | Amount | Preferred Amount | Most-Preferred Amount |
|---|---|---|---|
| valerian extract | 0.1-10 | 0.2-7 | 0.25-5 |
| water | 50-95 | 60-80 | 65-75 |
| ethanol | 5-20 | 7.5-15 | 9.5-12.5 |
| polyethylene glycol | 5-20 | 7.5-15 | 9.5-12.5 |
| flavors | 1-10 | 2-8 | 3-6 |

C. Echinacea as Bite Capsule

| | Amount | Preferred Amount | Most-Preferred Amount |
|---|---|---|---|
| *echinacea* extract | 30-85 | 40-75 | 45-55 |
| soya oil | 7.5-50 | 10-40 | 12.5-35 |
| soya lecithin | 0.001-1.0 | 0.005-0.5 | .01-0.1 |
| Soya fats | 7.5-50 | 10-40 | 12.5-35 |
| flavors | 1-10 | 2-8 | 3-6 |

D. Mixtures of Ingredients

| | Amount | Preferred Amount | Most-Preferred Amount |
|---|---|---|---|
| magnesium oxide | 15-40 | 20-35 | 25-30 |
| chromium picolinate | 0.01-1.0 | 0.02-0.5 | .025-0.75 |
| folic acid | .025-3.0 | 0.05-2.0 | 0.25-0.5 |
| vitamin B-12 | 0.01-1.0 | 0.02-0.5 | .025-0.75 |
| vitamin E | 15-40 | 20-35 | 25-30 |
| Soya oil | 10-40 | 12.5-35 | 15-20 |
| soya lecithin | 0.1-5 | 0.2-4 | 0.5-1.5 |
| soya fat | 10-40 | 15-35 | 17.5-20 |

Example 10

Sleep Inducers (Also CNS Active Amine)

A. Diphenhydramine Hydrochloride Lingual Spray

| | Amount | Preferred Amount | Most-Preferred Amount |
|---|---|---|---|
| diphenhydramine HCl | 3-50. | 4-40 | 5-35 |
| water | 5-90 | 10-80 | 50-75 |
| ethanol | 1-80 | 3-50 | 5-10 |
| polyethylene glycol | 1-80 | 3-50 | 5-15 |
| Sorbitol | 0.1-5 | 0.2-4 | 0.4-1.0 |
| aspartame | 0.01-0.5 | 0.02-0.4 | 0.04-0.1 |
| flavors | 0.1-5 | 1-4 | 2-3 |

Example 11

Anti-Asthmatics-Bronchodilators

A. Isoproterenol Hydrochloride as Polar Lingual Spray

| | Amount | Preferred Amount | Most-Preferred Amount |
|---|---|---|---|
| isoproterenol Hydrochloride | 0.1-10 | 0.2-7.5 | 0.5-6 |
| water | 5-90 | 10-80 | 50-75 |
| ethanol | 1-80 | 3-50 | 5-10 |
| polyethylene glycol | 1-80 | 3-50 | 5-15 |
| Sorbitol | 0.1-5 | 0.2-4 | 0.4-1.0 |
| aspartame | 0.01-0.5 | 0.02-0.4 | 0.04-0.1 |
| flavors | 0.1-5 | 1-4 | 2-3 |

B. Terbutaline Sulfate as Polar Lingual Spray

| | Amount | Preferred Amount | Most-Preferred Amount |
|---|---|---|---|
| terbutaline sulfate | 0.1-10 | 0.2-7.5 | 0.5-6 |
| water | 5-90 | 10-80 | 50-75 |
| ethanol | 1-10 | 2-8 | 2.5-5 |
| Sorbitol | 0.1-5 | 0.2-4 | 0.4-1.0 |
| aspartame | 0.01-0.5 | 0.02-0.4 | 0.04-0.1 |
| flavors | 0.1-5 | 1-4 | 2-3 |

C. Terbutaline as Non-Polar Lingual Spray

| | Amounts | preferred amount | most preferred amount |
|---|---|---|---|
| terbutaline | 0.1-10 | 0.2-7.5 | 0.5-6 |
| MIGLYOL ® | 25-50 | 30-45 | 35-40 |
| isobutane | 5-60 | 10-50 | 20-35 |
| polyoxyethylated oleic glycerides | 25-50 | 30-45 | 35-40 |
| flavors | 0.1-10 | 1-8 | 5-7.5 |

D. Theophylline Polar Bite Capsule

| | Amount | Preferred Amount | Most-Preferred Amount |
|---|---|---|---|
| theophylline | 5-50 | 10-40 | 15-30 |
| polyethylene glycol | 20-60 | 25-50 | 30-40 |
| glycerin | 25-50 | 35-45 | 30-40 |
| propylene glycol | 25-50 | 35-45 | 30-40 |
| flavors | 0.1-5 | 1-4 | 2-3 |

E. Albuterol Sulfate as Polar Lingual Spray

| | Amount | Preferred Amount | Most-Preferred Amount |
|---|---|---|---|
| albuterol sulfate | 0.1-10 | 0.2-7.5 | 0.5-6 |
| water | 5-90 | 10-80 | 50-75 |
| ethanol | 1-10 | 2-8 | 2.5-5 |
| Sorbitol | 0.1-5 | 0.2-4 | 0.4-1.0 |
| aspartame | 0.01-0.5 | 0.02-0.4 | 0.04-0.1 |
| flavors | 0.1-5 | 1-4 | 2-3 |

Example 12

Polar Solvent Formulations Using a Propellant

A. Sulfonylurea

|  | Amount | Preferred Amount | Most-Preferred Amount |
|---|---|---|---|
| glyburide | 0.1-25% | 0.5-15% | 0.6-10% |
| Ethanol | 40-99% | 60-97% | 70-97% |
| Water | 0.01-5% | 0.1-4% | 0.2-2% |
| Flavors | 0.05-10% | 0.1-5% | 0.1-2.5% |
| Propellant | 2-10% | 3-5% | 3-4% |

B. Prostaglandin E (Vasodilator)

|  | Amount | Preferred Amount | Most-Preferred Amount |
|---|---|---|---|
| prostaglandin $E_1$ | 0.01-10% | 0.1-5% | 0.2-3% |
| Ethanol | 10-90% | 20-75% | 25-50% |
| Propylene glycol | 1-90% | 5-80% | 10-75% |
| Water | 0.01-5% | 0.1-4% | 0.2-2% |
| Flavors | 0.05-10% | 0.1-5% | 0.1-2.5% |
| Propellant | 2-10% | 3-5% | 3-4% |

C. Promethazine (Antiemetic, Sleep Inducer, and CNS Active Amine)

|  | Amount | Preferred Amount | Most-Preferred Amount |
|---|---|---|---|
| promethazine | 1-25% | 3-15% | 5-12% |
| Ethanol | 10-90% | 20-75% | 25-50% |
| Propylene glycol | 1-90% | 5-80% | 10-75% |
| Water | 0.01-5% | 0.1-4% | 0.2-2% |
| Flavors | 0.05-10% | 0.1-5% | 0.1-2.5% |
| Propellant | 2-10% | 3-5% | 3-4% |

D. Meclizine

|  | Amount | Preferred Amount | Most-Preferred Amount |
|---|---|---|---|
| meclizine | 1-25% | 3-15% | 5-12% |
| Ethanol | 1-15% | 2-10% | 3-6% |
| Propylene glycol | 20-98% | 5-90% | 10-85% |
| Water | 0.01-5% | 0.1-4% | 0.2-2% |
| Flavors | 0.05-10% | 0.1-5% | 0.1-2.5% |
| Propellant | 2-10% | 3-5% | 3-4%. |

What is claimed is:

1. A propellant free oral spray composition for transmucosal administration of ondansetron or a pharmaceutically acceptable salt thereof comprising:

ondansetron or a pharmaceutically acceptable salt thereof in an amount of between 0.01 and 40 percent by weight of the total composition; and a mixture of a polar solvent and a non-polar solvent in an amount between 60.9 and 97.06 percent by weight of the total composition, wherein the non-polar solvent is selected from the group consisting of ($C_2$-$C_{24}$) fatty acid ($C_2$-$C_6$) esters, $C_7$-$C_{18}$ hydrocarbons of linear or branched configuration, $C_2$-$C_6$ alkanoyl esters, and triglycerides of $C_2$-$C_6$ carboxylic acids.

2. The composition of claim 1, wherein the polar solvent is selected from the group consisting of: polyethyleneglycols having a molecular weight between 400 and 1000, $C_2$ to $C_8$ mono- and poly-alcohols, and $C_7$ to $C_{18}$ alcohols of linear or branched configuration.

3. The composition of claim 1, wherein the polar solvent and non-polar solvents are present in a ratio of polar solvent to non-polar solvent of 1:99 to 99:1, 60:40 to 40:60, or 50:50.

* * * * *